United States Patent
Jensen et al.

(10) Patent No.: US 11,724,082 B2
(45) Date of Patent: Aug. 15, 2023

(54) FLUID LINE CONNECTORS

(71) Applicant: Fresenius Medical Care Holdings, Inc., Waltham, MA (US)

(72) Inventors: Lynn E. Jensen, Syracuse, UT (US); Melvin D. Jensen, West Haven, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 941 days.

(21) Appl. No.: 16/272,194

(22) Filed: Feb. 11, 2019

(65) Prior Publication Data
US 2019/0167968 A1 Jun. 6, 2019

Related U.S. Application Data

(63) Continuation of application No. 13/778,655, filed on Feb. 27, 2013, now Pat. No. 10,207,096.

(51) Int. Cl.
*A61M 39/10* (2006.01)

(52) U.S. Cl.
CPC .. *A61M 39/1011* (2013.01); *A61M 2039/1033* (2013.01)

(58) Field of Classification Search
CPC ...... A61M 39/1011; A61M 2039/1033; A61M 39/10; A61M 2039/1066; A61M 39/165; H01R 4/28; H01R 4/5008; H01R 4/5033; H01R 4/5041; H01R 4/505
See application file for complete search history.

(56) References Cited

U.S. PATENT DOCUMENTS

| 3,986,508 A | 10/1976 | Barrington |
| 4,211,439 A | 7/1980 | Moldestad |
| 4,407,619 A | 10/1983 | Siebol |

(Continued)

FOREIGN PATENT DOCUMENTS

| EP | 0453264 | 10/1991 |
| WO | WO 95/22369 | 8/1995 |

(Continued)

OTHER PUBLICATIONS

PCT International Preliminary Report on Patentability in International Appln. No. PCT/US2014/016890, dated Sep. 11, 2015, 8 pages.

(Continued)

*Primary Examiner* — Kevin C Sirmons
*Assistant Examiner* — William R Frehe
(74) *Attorney, Agent, or Firm* — Fish & Richardson P.C.

(57) ABSTRACT

A male luer connector includes a body having a first end configured to be connected to a fluid line, a second end opposed to the first end, and a body longitudinal axis. The second end is configured to be inserted into and form a luer slip connection with a female luer connector. The male luer connector also includes a locking collar that is connected to the body in a manner such that the locking collar rotates about the longitudinal axis. In some cases, the body second end does not protrude beyond a plane that is transverse to the longitudinal axis and that includes an end face of the locking collar, and/or when male and female connectors are engaged, the locking collar engages an outer surface of the female fluid line connector and is deformed by the engagement.

15 Claims, 7 Drawing Sheets

(56) References Cited

U.S. PATENT DOCUMENTS

| | | | |
|---|---|---|---|
| 4,439,188 A * | 3/1984 | Dennehey | A61J 1/00 604/534 |
| 4,511,359 A | 4/1985 | Vaillancourt | |
| 4,616,953 A | 10/1986 | Gomes | |
| 4,735,441 A | 4/1988 | Stephens | |
| 5,201,717 A | 4/1993 | Wyatt et al. | |
| 5,292,308 A | 3/1994 | Ryan | |
| 5,466,020 A | 11/1995 | Page et al. | |
| 5,509,911 A * | 4/1996 | Cottone, Sr. | A61M 39/1055 604/905 |
| 5,526,956 A * | 6/1996 | Osgar | B67D 7/76 222/105 |
| 5,620,427 A | 4/1997 | Werschmidt et al. | |
| 5,632,651 A | 5/1997 | Szegda | |
| 5,658,260 A | 8/1997 | Desecki et al. | |
| 5,707,086 A | 1/1998 | Treu et al. | |
| 5,709,413 A | 1/1998 | Salyers | |
| 5,830,195 A | 11/1998 | Peters et al. | |
| 5,934,937 A * | 8/1999 | McCarthy | H01R 4/5033 439/583 |
| 6,152,913 A * | 11/2000 | Feith | A61M 39/1011 604/533 |
| 6,382,442 B1 | 5/2002 | Thibault et al. | |
| 6,402,207 B1 | 6/2002 | Segal et al. | |
| 6,612,624 B1 | 9/2003 | Segal et al. | |
| 6,893,056 B2 * | 5/2005 | Guala | F16L 47/04 285/332.1 |
| 7,056,308 B2 | 6/2006 | Utterberg | |
| 7,569,047 B2 | 8/2009 | Utterberg | |
| 7,699,645 B1 | 4/2010 | Montena et al. | |
| 8,070,189 B2 | 12/2011 | Yow et al. | |
| 8,202,495 B1 | 6/2012 | Smith | |
| 8,257,287 B2 | 9/2012 | Hanlon et al. | |
| 8,287,517 B2 | 10/2012 | Hanlon et al. | |
| 8,613,731 B2 | 12/2013 | Hansen et al. | |
| 8,684,979 B2 | 4/2014 | Deighan et al. | |
| 8,777,931 B2 * | 7/2014 | Davis | A61M 39/10 285/332 |
| 2001/0010738 A1 | 8/2001 | Johnson et al. | |
| 2002/0115984 A1 * | 8/2002 | Guala | A61M 39/1011 604/533 |
| 2003/0040720 A1 * | 2/2003 | Steube | A61M 5/34 604/240 |
| 2003/0083730 A1 | 5/2003 | Stinson | |
| 2005/0143828 A1 * | 6/2005 | Collins | A61F 2/36 623/18.11 |
| 2006/0178627 A1 * | 8/2006 | Geiger | A61M 5/3134 215/250 |
| 2007/0016166 A1 | 1/2007 | Thistle | |
| 2008/0188816 A1 | 8/2008 | Shimazaki et al. | |
| 2008/0228258 A1 | 9/2008 | Gerdts et al. | |
| 2009/0177186 A1 | 7/2009 | Delano | |
| 2012/0104744 A1 | 5/2012 | Petty | |
| 2012/0209206 A1 | 8/2012 | Scandone, Jr. | |
| 2013/0046287 A1 | 2/2013 | Davis et al. | |
| 2013/0079730 A1 | 3/2013 | Mosler et al. | |
| 2013/0158521 A1 | 6/2013 | Sobue | |
| 2013/0270820 A1 | 10/2013 | Py | |
| 2015/0001845 A1 | 1/2015 | Penny et al. | |

FOREIGN PATENT DOCUMENTS

| | | |
|---|---|---|
| WO | WO 02/066100 | 8/2002 |
| WO | WO 2009/024007 | 2/2009 |
| WO | WO 2009/024807 | 2/2009 |
| WO | WO 2015/067359 | 5/2015 |

OTHER PUBLICATIONS

"Conical fittings with 6% {luer} taper for syringes, needles and certain other medical equipment—Part 2: Lock Fittings" International Organization for Standardization, reference No. ISO 594-2:1998(e), 1998, 16 pages.

Notification of Transmittal of the International Search Report and The Written Opinion of the International Search Authority for corresponding PCT Application No. PCT/US2014/016890, dated May 13, 2014, 10 pages.

* cited by examiner

FLUID LINE CONNECTORS

CROSS-REFERENCE TO RELATED APPLICATIONS

This application is a continuation application of and claims priority to U.S. application Ser. No. 13/778,655, filed on Feb. 27, 2013.

TECHNICAL FIELD

This disclosure relates to fluid line connectors.

BACKGROUND

Dialysis is a treatment used to support a patient with insufficient renal function. During hemodialysis, the patient's blood is passed through an extracorporeal hemodialysis circuit that includes a dialysis machine. In particular, the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

In hemodialysis and many other medical procedures, luer connectors are used to obtain leak-free connections in fluid lines between a male fitting and a corresponding female fitting. For example, luer connectors are used to connect fluid lines to needles, syringes, catheters, fluid reservoirs, laboratory instruments, and other medical devices. In hemodialysis treatments in particular, male luer connectors are used to connect the flexible tubing of an extracorporeal blood circuit to and from a female luer connector that accesses a patient's circulatory system during the dialysis treatment.

SUMMARY

In some aspects, a male fluid line connector is configured to engage a female fluid line connector. The male fluid line connector includes a body having a first end configured to be connected to a fluid line, a tapered second end opposed to the first end, the second end configured to be inserted into and form a fluid-tight connection with the female fluid line connector, and a body longitudinal axis that extends between the first end and the second end. The male fluid line connector also includes a locking collar having a locking collar first end, and a locking collar second end opposed to the locking collar first end. The locking collar first end is connected to the body in a manner such that the locking collar can rotate about the longitudinal axis, and the locking collar is configured such that when the second end of the body is inserted into the female fluid line connector, the locking collar second end engages an outer surface of the female fluid line connector and is deformed by the engagement.

In some implementations, the locking collar includes internal threads that engage corresponding threads provided on the outer surface of the female fluid line connector, and the locking collar internal threads deform when engaged with the threads provided on the outer surface of the female fluid line connector.

In some implementations, the locking collar internal threads have a thread angle that is greater than a thread angle of the threads provided on the outer surface of the female fluid line connector.

In some implementations, a major diameter of the locking collar internal threads is less than a major diameter of the threads provided on the outer surface of the female fluid line connector.

In some implementations, the locking collar is more flexible than the female fluid line connector.

In some implementations, the locking collar is formed of a material that is more flexible than the material used to form the female fluid line connector.

In some implementations, the locking collar has a durometer value that is less than the durometer value of the female fluid line connector on a given durometer scale.

In some implementations, the locking collar includes through holes that are elongated in a direction parallel to the longitudinal axis.

In some implementations, an interior surface of the locking collar includes a region that engages a region of the outer surface of the female fluid line connector, and the region of the locking collar has a maximum inner diameter that is less than the maximum outer diameter of the female fluid line connector region.

In some implementations, each through holes is spaced apart from the adjacent through holes along a circumference of the locking collar.

In some implementations, the body is formed of a material having a first coefficient of friction and the locking collar is formed of a material having a second coefficient of friction, and the first coefficient of friction is less than that of the second coefficient of friction.

In some implementations, the first coefficient of friction has a range of 0.1 to 0.3.

In some implementations, the second end of the body does not protrude beyond a plane that is transverse to the longitudinal axis and includes an end face of the locking collar.

In some implementations, the internal threads of the locking collar are arranged to begin at a predetermined distance from the locking collar end face, and the predetermined distance is selected so that when the second end of the body is inserted into the female fluid line connector, a leading edge of threads provided on the outer surface of the female fluid line connector abuts a leading edge of the internal threads of the locking collar before an outer surface of the second end of the body forms a connection with an internal surface of the female fluid line connector.

In some implementations, the second end of the body is recessed within the locking collar.

In some implementations, the second end of the body is recessed within the locking collar by 0.5 mm to 2 mm.

In some implementations, the second end of the body is configured to form a luer-slip connection with the female fluid line connector.

In some aspects, a male fluid line connector is configured to engage a female fluid line connector. The male fluid line connector includes a body having a first end configured to be connected to a fluid line, a tapered second end opposed to the first end, the second end configured to be inserted into and form a fluid-tight connection with the female fluid line connector, and a body longitudinal axis that extends between the first end and the second end. The male fluid line connector also includes a locking collar having a locking collar first end configured to engage the body so as to rotate relative to the body about the longitudinal axis and a locking collar second end configured to receive the female fluid line connector. The second end of the body does not protrude beyond a plane that is transverse to the longitudinal axis and includes the locking collar second end.

In some implementations, the second end of the body is recessed within the locking collar.

In some implementations, the locking collar second end is aligned with the second end of the body when viewed in a direction perpendicular to the longitudinal axis.

In some implementations, when the second end of the body is inserted into the female fluid line connector, the locking collar engages an outer surface of the female fluid line connector in such a way that the locking collar is deformed.

In some implementations, the locking collar includes internal threads that engage corresponding threads provided on the outer surface of the female fluid line connector, and the locking collar internal threads deform when engaged with the threads provided on the outer surface of the female fluid line connector.

In some implementations, the locking collar internal threads have a thread angle that is greater than a thread angle of the threads provided on the outer surface of the female fluid line connector.

In some implementations, a major diameter of the locking collar internal threads is less than a major diameter of the threads provided on the outer surface of the female fluid line connector.

In some implementations, the locking collar is more flexible than the female fluid line connector.

In some implementations, the locking collar is formed of a material that is more flexible than the material used to form the female fluid line connector.

In some implementations, the locking collar has a durometer value that is less than the durometer of the female fluid line connector on a given durometer scale.

In some implementations, the locking collar includes through holes that are elongated in a direction parallel to the longitudinal axis.

In some implementations, an interior surface of the locking collar includes a region that engages a region of the outer surface of the female fluid line connector, and the locking collar region has a maximum inner diameter that is less than the maximum outer diameter of the female fluid line connector region.

In some implementations, each through hole is spaced apart from the adjacent through holes along a circumference of the locking collar.

In some implementations, the body is formed of a material having a first coefficient of friction and the locking collar is formed of a material having a second coefficient of friction, and the first coefficient of friction is less than that of the second coefficient of friction.

In some implementations, the first coefficient of friction has a range of 0.1 to 0.3.

In some implementations, the second end is configured to form a luer-slip connection with the female fluid line connector.

In some aspects, a male fluid line connector is configured to engage a female fluid line connector. The male fluid line connector includes a body having a first end configured to be connected to a fluid line, a tapered second end opposed to the first end, the second end configured to be inserted into and form a fluid-tight connection with the female fluid line connector, and a body longitudinal axis that extends between the first end and the second end. The male fluid line connector also includes a locking collar having a locking collar first end, and a locking collar second end opposed to the locking collar first end. The locking collar first end is connected to the body in a manner such that the locking collar rotates about the longitudinal axis, the locking collar includes internal threads that are configured to engage corresponding threads provided on the female fluid line connector outer surface, and the locking collar internal threads deform when engaged with the threads provided on the female fluid line connector outer surface, the locking collar is more flexible than the female fluid line connector, the body is formed of a material having a first coefficient of friction and the locking collar is formed of a material having a second coefficient of friction that is greater than that of the second coefficient of friction, and the second end of the body does not protrude beyond a plane that is transverse to the longitudinal axis and includes the locking collar second end.

A male luer connector is described that provides improved connection security relative to some conventional male luer connectors that include a threaded, rotating locking collar used to secure the collar to mating threads on a corresponding female luer connector. The locking collar is intended to provide additional security to the male-to-female luer connection. However, in some conventional male luer connectors, inadvertent disconnection between male and female luer connectors can occur if a rotational force is applied to the male luer connector and the female luer connector independent of the collar. For example, torque applied to the male and female luer connectors by the fluid line tubing can cause the locking collar to unscrew and allow the male-to-female luer connection to separate. An advertent disconnection can also occur if the male and female luer tapers are engaged without properly securing the locking collar of the male luer connector to the female luer connector threads. Security of the connection between the male luer connector and the corresponding female luer connector is particularly important in some medical procedures and/or treatments since if the connection fails during treatment, a potentially fatal problem can arise. For example, if the mail luer connector inadvertently becomes disconnected from the female luer connector on the venous side of a hemodialysis blood circuit, the patient can quickly become exsanguinated.

In some implementations, the male luer connector includes a locking collar that is configured to be more compliant than the female luer connector. The relative compliance can be achieved through appropriate selection of materials used to form the locking collar and female luer connector. Alternatively, it can be achieved by providing the locking collar with physical features, such as longitudinally-extending slits, that allow the locking collar to deform more easily than the female luer connector. Since the locking collar is more compliant than the female luer connector, the locking collar can secure the connection between the male luer connector body and the female luer connector regardless of dimensional variations in either the locking collar or the threads of the female luer connector, while maintaining a slight friction between the male and female luer threads.

In some implementations, the locking collar includes internal threads having dimensions that are designed to provide a slight interference with the external threads of the female luer connector. Advantageously, this feature can permit the locking collar internal threads to remain engaged with the external threads of the female luer connector even when the fluid lines extending from each of the male and female luer connectors are counter-rotated.

In some implementations, the male luer connector body is formed of a material having a lower coefficient of friction than that of the material used to form the locking collar. This configuration can allow the male luer connector body to rotate relative to the locking collar without imparting a rotational force to the locking collar. This can in turn prevent the locking collar internal threads from disengaging from the external threads of the female luer connector even when the fluid lines extending from each of the male and female luer connectors are counter-rotated.

In some implementations, the luer tip of the male luer connector body is slightly recessed within the locking collar. As a result, the locking collar internal threads must be engaged with the external threads of the female luer connector in order to achieve engagement and sealing between the luer tip of the male luer connector body and the luer socket of the female luer connector. Thus, it is ensured that both the locking collar and luer tip are securely engaged with the female luer connector during use. This is advantageous relative to conventional male luer connector configurations including a luer tip that protrudes beyond an end of the locking collar. In such conventional connectors, since the luer tip protrudes beyond an end of the locking collar, it is possible to obtain a connection between the luer tip and the socket portion of the female luer connector without obtaining an engagement of the locking collar with the external threads of the female luer connector. In some cases, it is possible to overlook that the locking collar has not been engaged, whereby the resulting connection can be insecure and easily disconnected.

Other aspects, features, and advantages will be apparent from the description and drawings, and from the claims.

DETAILED DESCRIPTION

Figure 1:
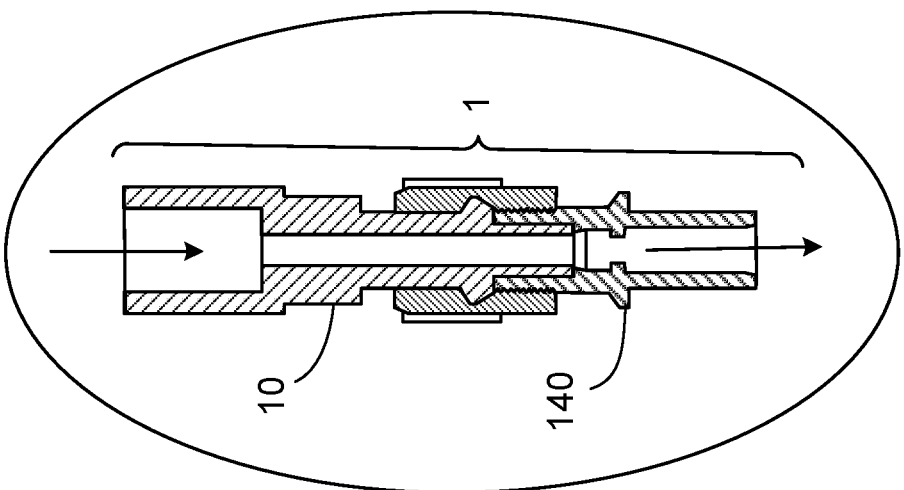
FIG. 1 is a schematic illustration of an extracorporeal hemodialysis circuit including a male-to-female luer connection that joins a fluid line of the extracorporeal hemodialysis circuit to a patient catheter.
Figure 1:
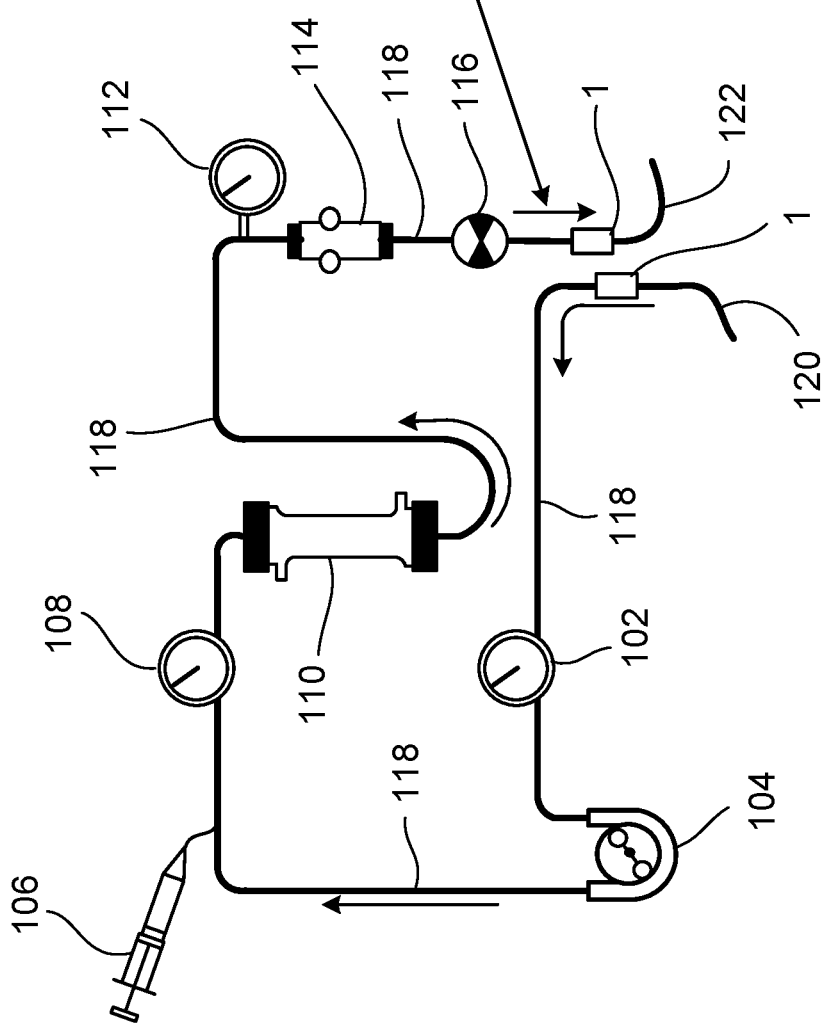

Referring to FIG. 1, an extracorporeal hemodialysis circuit 100 includes a flexible tubing fluid line 118 connected to a patient catheter assembly 120 via a first male-to-female luer connection 1. The fluid line 118 receives arterial blood removed from the patient via the first male-to-female luer connection 1 and the patient catheter assembly 120. The fluid line 118 conveys the blood to an arterial blood pressure monitor 102, a blood pump 104, such as a peristaltic pump, a pressure sensor 108 that monitors dialyzer inflow pressure, and then to the dialyzer 110. After the blood is filtered within the dialyzer 110, the fluid line 118 conveys the blood to a pressure sensor 112 that monitors venous blood pressure, through an air trap/detector device 114, a valve 116, and back to a vein of the patient via another patient catheter assembly 122 that is connected to the fluid line 118 by a second male-to-female luer connection 1.

Figure 2:
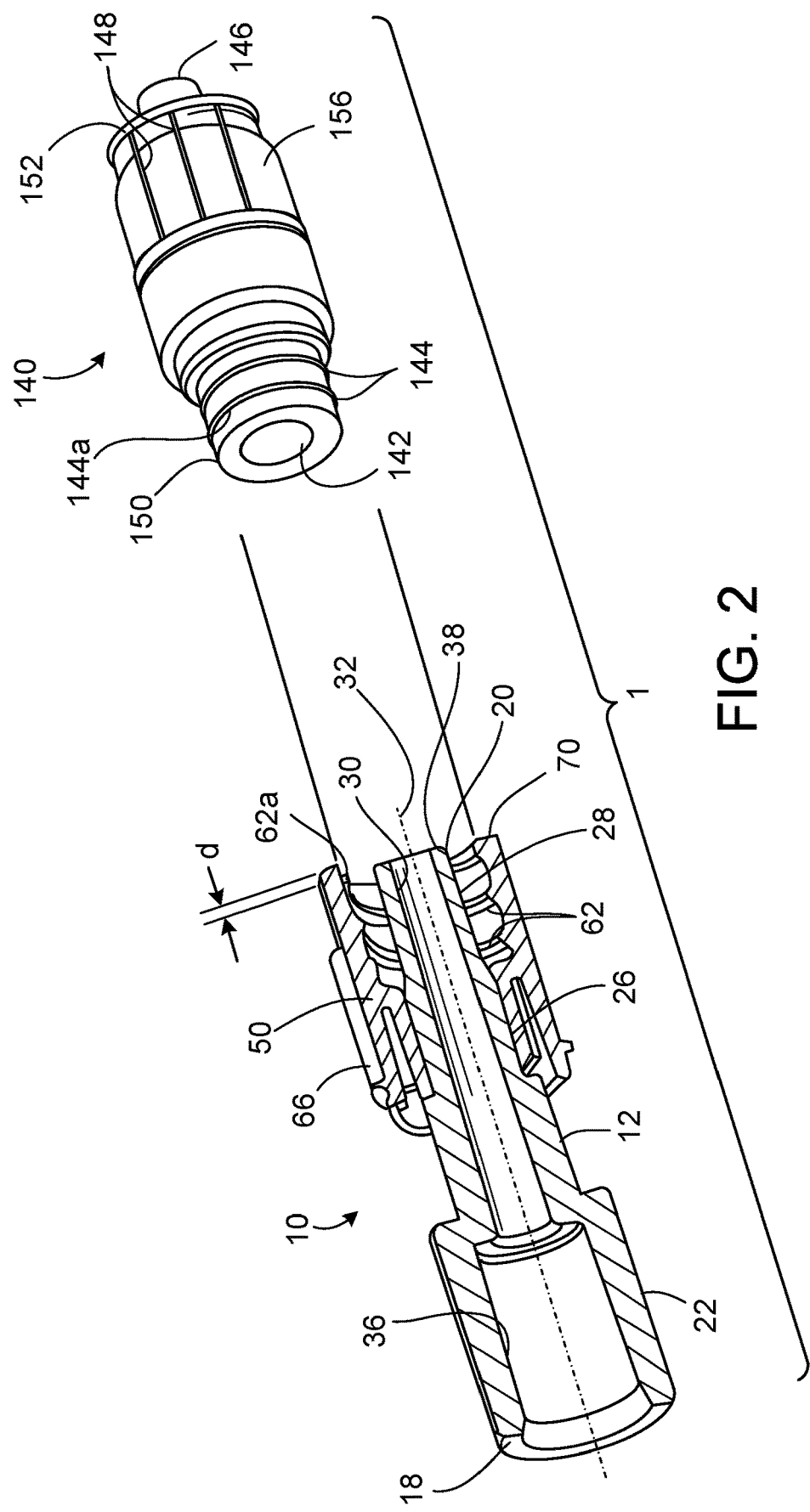
FIG. 2 is a partially cut away exploded perspective view of the male-to-female luer connection of FIG. 1.

Referring to FIG. 2, the male-to-female luer connection 1 includes a male luer connector 10 and a female luer connector 140. The male luer connector 10 is configured to engage the female luer connector 140 to obtain a leak-free connection. The male luer connector 10 includes a luer tip 28 having a tapered outer surface that is press fit within a correspondingly-tapered socket 142 of the female luer connector 140. This connection is referred to as a luer-slip connection. In some embodiments, the taper is a 6 percent taper, and the luer-slip connection along the tapered surfaces is maintained by friction. To ensure that the luer-slip connection is maintained, the male luer connector 10 also engages an outer surface of the female luer connector 140. In particular, the male luer connector 10 includes a locking collar 50 having internal threads 62 that are configured to engage external threads 144 provided on the female luer connector 140, as further discussed below.

The female luer connector 140 is a tubular member having a first end 150 that engages the male luer connector 10, and a second end 152 opposed to the first end 150. The second end 152 includes a tubing connection portion 146 that permits the female luer connector 140 to be connected to a fluid line (e.g., fluid line 118). Between the first end 150 and the second end 152, the outer surface 156 of the female luer connector 140 is provided with finger grips 148 to facilitate manual gripping of the female luer connector 140. The female luer connector first end 150 includes the socket 142 defining a conical inner surface that has an inward 6 percent (Luer) taper so as to be widest at the connector first end 150. The socket 142 is in fluid communication with the tubing connection portion 146, providing a fluid flow passageway through the female luer connector 140. The outer surface of the female luer connector first end 150 is provided with the external threads 144 that engage the internal threads 62 of the male luer connector 10. The tapered socket 142 and external threads 144 are shaped and dimensioned according to requirements specified in industry standards, for example the international standard ISO 594-2: 1998(E), "Conical Fittings with 6% (Luer) Taper For Syringes, Needles and Certain Other Medical Equipment, Part 2: Lock Fittings," Second Edition, 1998 Sep. 1, the contents of which are incorporated herein by reference.

Figure 3:
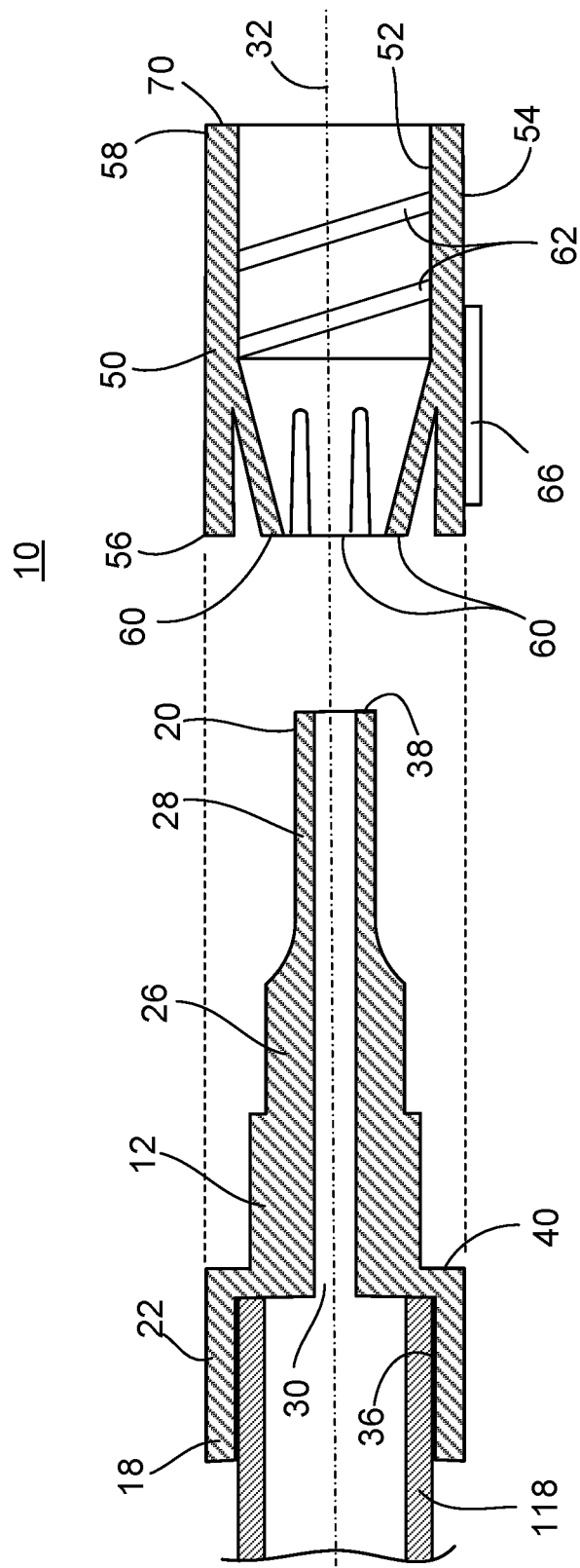
FIG. 3 is an exploded side sectional view of the male luer connector of FIG. 1.
Figure 4:
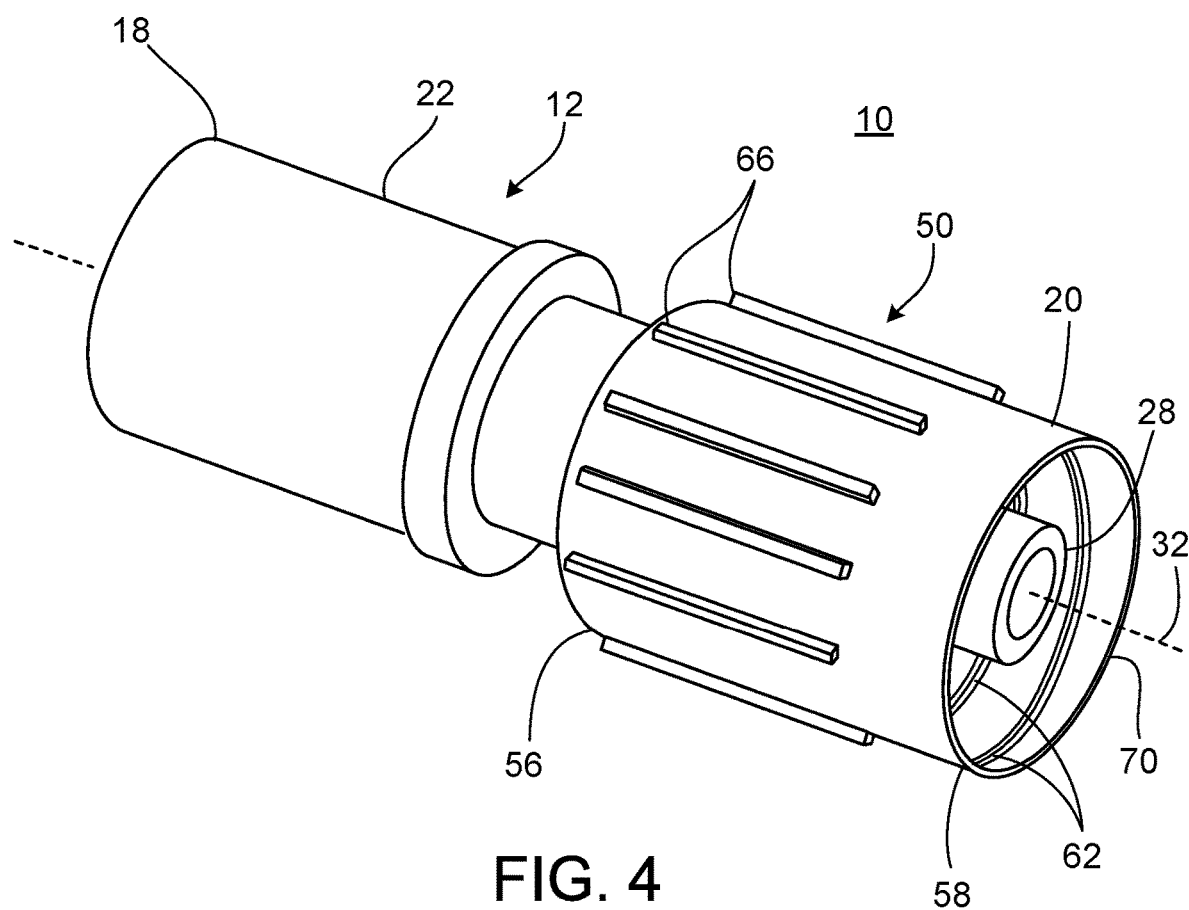
FIG. 4 is a perspective view of the male luer connector of FIG. 1.

Referring to FIGS. 3 and 4, the male luer connector 10 includes a connector body 12 and the locking collar 50 that is rotatably connected to the connector body 12, as discussed below. The connector body 12 is a generally cylindrical tube that has a first end 18, a second end 20 opposed to the first end 18, and a longitudinal axis 32 that extends between the first end 18 and the second end 20. The male luer connector first end 18 includes a tubing connection portion 22 that permits the male luer connector 10 to be connected to a fluid line (e.g., fluid line 118). In the illustrated embodiment, the tubing connection portion 22 has an enlarged diameter relative to that of the body 12, and includes an opening 36 dimensioned to receive an end of a fluid line therein. In some embodiments, the fluid line is press fit within the opening 36 and retained within the opening 36 via friction. In other embodiments, the fluid line may be retained within the opening 36 using adhesives, by welding, etc.

The connector body 12 includes a collar seat 26 disposed between the first end 18 and the second end 20 at a location spaced apart from the tubing connection portion 22 along the longitudinal axis 32. The collar seat 26 is configured to receive and retain a first end 56 of the locking collar 50. In particular, the collar seat 26 is a region of reduced outer diameter relative to an outer diameter of the body 12, whereby a shoulder 40 is formed at one end of the collar seat 26. In addition, the outer surface of the connector body 12 is tapered in the vicinity of the collar seat 26 so that the collar seat 26 has a minimum outer dimension at the shoulder 40 and a maximum outer dimension adjacent the luer tip 28. The reduced diameter and tapered configuration of the collar seat 56 facilitates retention of the locking collar 50 on the connector body 12, as discussed further below.

The male luer connector second end 20 includes the luer tip 28, which extends between the collar seat 26 and an end face 38 of the connector body 12. The luer tip 28 has a conical outer surface that has an inward 6 percent (Luer) taper. In particular, the luer tip 28 has a maximum outer dimension adjacent the collar seat 26 and a minimum outer dimension at the end face 38. This configuration corresponds to the shape and dimensions of the female luer connector socket 142 such that a leak-free luer slip connection can be formed when the luer tip 28 is press fit within the socket 142 of the female luer connector 140. In some implementations, leak-free refers to a liquid-tight connection. In other implementations, leak-free refers to a fluid-tight connection. The male luer connector 10 includes an internal fluid passageway 30 that extends longitudinally and provides fluid communication between the tubing connection portion 22 and the end face 38.

The locking collar 50 is a hollow cylinder that includes a first end 56 and a second end 58 that is opposed to the first end 56. Finger grips 66 are provided on the outer surface 54 of the locking collar 50 adjacent to the locking collar first end 56. The finger grips 66 improve manual gripping of the locking collar 50. In the illustrated embodiment, the finger grips 66 are outwardly-protruding elongated ribs that extend in parallel to the longitudinal axis 32. The ribs are provided at regular intervals about the circumference of the locking collar 50. In addition, internal threads 62 are provided on an inner surface 52 of the locking collar 50 adjacent to the locking collar second end 58. The internal threads 62 are configured to engage the external threads 144 of the female luer connector 140 and thereby provide a secure connection between the male fluid line connector 10 and the female fluid line connector 140.

As discussed above, the locking collar first end 56 is connected to the body 12 in a manner such that the locking collar 50 rotates about the longitudinal axis 32 and is prevented from movement along the direction of the longitudinal axis 32. To this end, resilient fingers 60 are formed on the inner surface 52 of the locking collar 50 adjacent to the first end 56. The fingers 60 protrude radially inward at an angle relative to the inner surface 52 and toward the locking collar first end 56. When the locking collar 50 is assembled with the body 12, the luer tip 28 is inserted into the locking collar first end 56 and through an opening defined by the free ends of the fingers 60 until the locking collar first end 56 abuts the shoulder 40. The fingers 60 are configured to pass over the body second end 20 including the luer tip 28 during assembly with minimal finger deflection. However, the fingers 60 are configured to be deflected outward (e.g. toward the collar inner surface 52) by the collar seat 26, whereby the fingers 60 are snap-fit on to and retained by the collar seat 26 via cooperation between the collar seat taper and the inwardly-directed resiliency of the fingers 60. The engagement of the resilient fingers 60 with the collar seat 26 substantially prevents longitudinal movement of the collar 50 relative to the body 12, while permitting the locking collar to rotate relative to the body 12 about the longitudinal axis 32.

Figure 5:
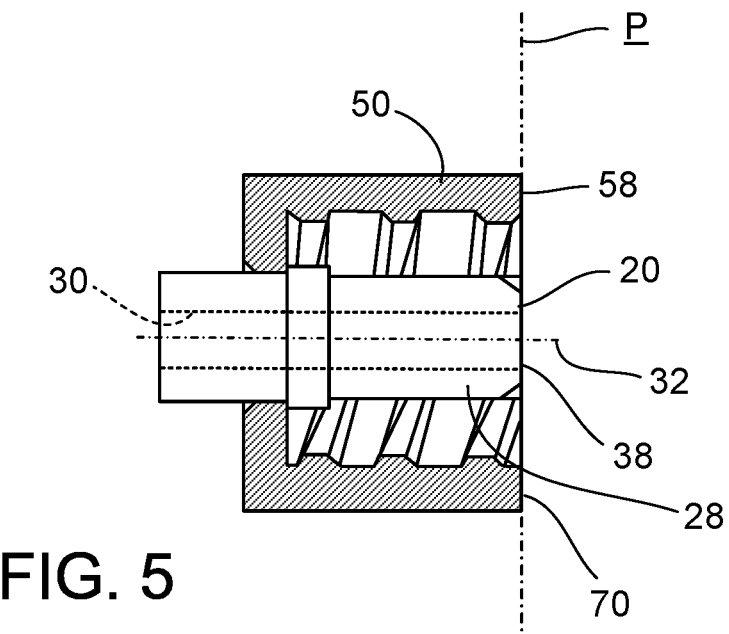
FIG. 5 is an enlarged view of the second end of the male luer connector of FIG. 1.
Figure 6:
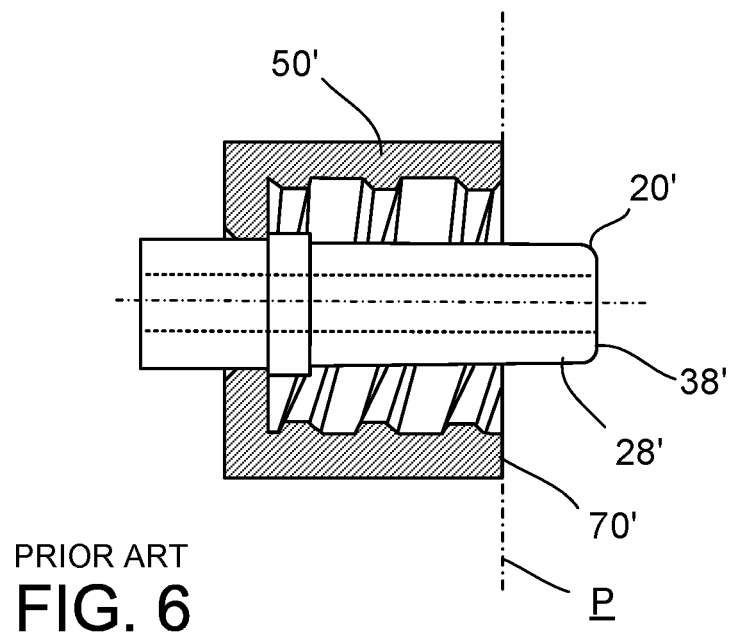
FIG. 6 is an enlarged view of the second end of a prior art male luer connector.

Referring to FIGS. 5 and 6, when the locking collar 50 is assembled with the body 12 such that the locking collar first end 56, including the resilient fingers 60, is disposed within the collar seat 26, the end face 38 of the connector body 12 does not protrude beyond a plane P that is transverse to the longitudinal axis 32 and includes an end face 70 of the locking collar 50 (FIG. 5). In some embodiments, the connector body end face 38 is recessed within the locking collar 50 relative to the plane P. For example, the connector body end face may be recessed within the locking collar 50 by 0.5 mm to 2 mm relative to the plane P. The configuration in which the end face 38 of the body second end 20 is recessed within the locking collar 50 can be compared to some conventional male luer connectors 10' in which the luer tip 28' including the end face 38' protrudes outward beyond the plane P (FIG. 6). In particular, male luer connectors formed according to ISO standard 594-2 have an end face 38' that protrudes 2.1 mm beyond the plane P. In such conventional male luer connectors 10', since the luer tip 28' protrudes outward, it is possible to obtain a luer slip connection between the luer tip 28' and the female luer connector socket without securing the locking collar 50' to the external threads of the female luer connector. For example, since the locking collar 50' overlies the external threads, it can appear to be secured even if the locking collar 50' has not yet been rotated to engage the external threads. However, by providing a male luer connector 10 in which the end face 38 of the connector body 12 does not protrude beyond the plane P, the locking collar 50 must be rotated in order to obtain engagement of locking collar internal threads 66 and the female luer connector external threads 144 before the luer slip connection between the luer tip 28 and the female luer connector socket 142 can be made. This arrangement helps to ensure that both the locking collar 50 and the luer tip 28 form a connection with the female luer connector 140, resulting in a reliable and secure male-to-female luer connection.

The male luer connector 10 may include other features to improve connection security between the male luer connector 10 and the female luer connector 140. In some aspects, the materials used to form the male luer connector 10 are selected so that the locking collar 50 rotates freely relative to the connector body 12. In particular, the materials of the connector body 12 and locking collar 50 are selected so that the locking collar fingers 60 rotate freely relative to the collar seat 26.

For example, in some embodiments, the body 12 is formed of a material having a coefficient of friction that is less than (e.g., about 0.2 to about 0.4 less than) the coefficient of friction of the material used to form the locking collar 50. In some embodiments, the body 12 is formed of acrylic including an additive of two percent polypropylene, whereby the body 12 has a coefficient of friction of 0.1. Other possible materials that may be used to form the body 12 include, but are not limited to, polypropylene, polyethylene, and polyester. In some embodiments, the coefficient of friction of the material used to form the body 12 is in the range of 0.1 to 0.3. This can be compared to the coefficient of friction of materials conventionally used to form fluid line connectors, including ABS and polyvinylchloride (PVC), having a coefficient of friction in a range of 0.2 to 0.5. In some embodiments, the locking collar 50 is formed of a common thermoplastic such as acrylonitrile butadiene styrene (ABS), having a coefficient of friction of 0.5.

By providing the body 12 of a material having a relatively low coefficient of friction compared to that of the locking collar 50, the locking collar 50 can rotate freely relative to the body 12. As a result, if a rotational force is applied to the body 12, it becomes difficult for the body 12 to transfer the rotational force to the locking collar 50, enhancing the security of the connection between the male luer connector 10 and the female luer connector 140.

In some embodiments, the internal threads 62 of the locking collar 50 are arranged to begin at a predetermined distance d from the locking collar end face 70. This distance d is selected so that when the second end 20 of the connector body 12 is inserted into the female fluid line connector 140, a leading edge 144a of threads provided on the outer surface of the female fluid line connector 140 abuts a leading edge 62a of the internal threads 62 of the locking collar 50 before the outer surface of the luer tip 28 of the body second end 20 forms a connection with female fluid connector socket 142.

This feature, in combination with selecting the materials used to form the male luer connector 10 so that the locking collar 50 rotates freely relative to the connector body 12, can prevent a user from connecting a female luer connector 140 to a male luer connector by merely inserting the second end 20 of the connector body 12 into the female fluid line connector 140 and rotating the female luer connector 140. Such a procedure can result in formation of a luer slip connection, but in some cases does not also result in a secure threaded engagement between the internal threads 62 of the locking collar 50 and the external threads 144 of the female luer connector 140. In addition, in such a procedure, the user may mistakenly assume that the rotation of the female luer connector was sufficient to achieve a secure connection between the internal threads 62 of the locking collar 50 and the external threads 144 of the female luer connector 140 since the female luer connector 140 is manually rotated relative to both the connector body 12 and locking collar 50. By providing the locking collar threads as described in combination with the with forming the locking collar 50 with a low coefficient of friction relative to that of the connector body 12, when the second end 20 of the connector body 12 is inserted into the female fluid line connector 140 and the female luer connector 140 is rotated, the locking collar 50 rotates in concert with the female luer connector 140. Since the locking collar 50 rotates together with the female luer connector 140, the internal threads 62 of the locking collar 50 do not engage the external threads 144 of the female luer connector 140. That is, connection between the male luer connector 10 and the female luer connector 140 is not made until the user manually rotates the locking collar 50, whereby the internal threads 62 of the locking collar 50 engage the external threads 144 of the female luer connector 140, and the male luer tip 28 is drawn into a luer-slip connection with the female socket 142.

To further improve connection security between the male luer connector 10 and the female luer connector 140, in some embodiments, the locking collar 50 is configured to be deformed when the male luer connector body second end 22 is inserted into the female fluid line connector 140. In particular, when the locking collar internal threads 62 engage the corresponding external threads 144 of the female luer connector 140, the locking collar internal threads 62 deform. The compliance of the locking collar 50 permits accommodation of dimensional variations between the locking collar 50 and the female luer connector 140, while maintaining a slight friction between the locking collar internal threads 62 and the female luer connector external threads 144. This friction allows the locking collar 50 to remain securely in place (e.g., the locking collar internal threads 62 remain securely engaged with the female luer connector external threads 144) if the male luer connector 10 is rotated relative to the female luer connector 10 during use.

In some embodiments, the locking collar 50 is formed to be more flexible than the the female luer connector 140 to allow the threads 62 to deform when engaged with the female luer connector external threads 144. The flexibility of a component depends on the flexibility of the material used to form the component, the component thickness and component shape. Thus, for implementations where the locking collar shape and thickness are maintained, the locking collar 50 is formed of a material that is more flexible than the material used to form the female luer connector 140 to allow the threads 62 to deform when engaged with the female luer connector external threads 144. For example, the locking collar 50 can be formed of polyethylene or polypropylene having a durometer value in the range of 55 to 70 Shore D, as compared to the female luer connector 140 which may be formed of ABS having a durometer value of about 75 Shore D. For example, in some embodiments, the locking collar 50 has a durometer value that is less than (e.g., about 5 to about 15 less than) the durometer value of the female luer connector 140 for a given durometer scale.

Figure 7:
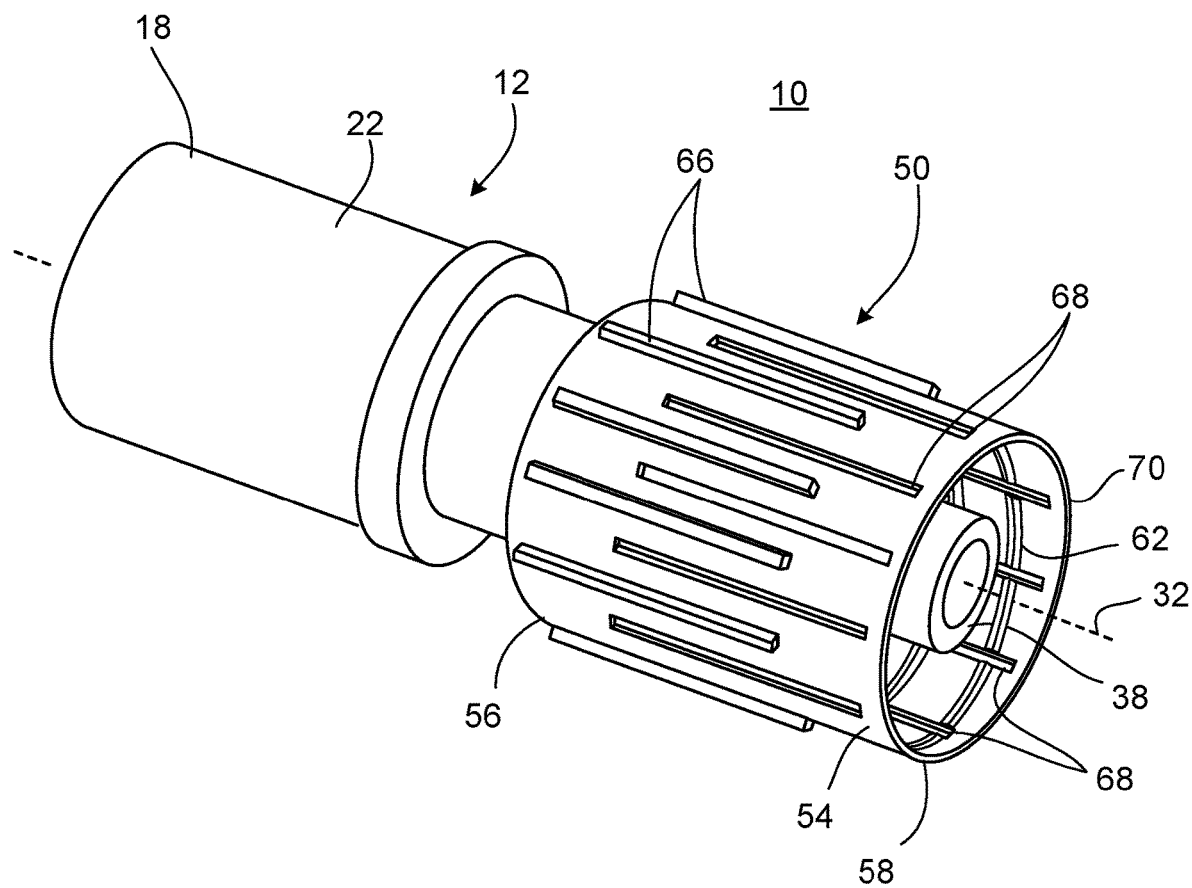
FIG. 7 is a perspective view of another male luer connector including a locking collar having axially elongated through holes.

In some embodiments, the locking collar 50 includes structural features that increase the compliance of the locking collar itself. For example, in the embodiment illustrated in FIG. 7, the locking collar 50 includes through holes 68 extending between the inner surface 52 and outer surface 54 of the locking collar 50. The through holes 68 are elongated in a direction parallel to the longitudinal axis 32, and reside adjacent the collar second end 58 so as to interrupt the internal threads 62. In addition, each through holes 68 is spaced apart from the adjacent through holes 68 along a circumference of the locking collar 50. Since the locking collar includes the through holes 68, the locking collar 50 can be more easily deformed during engagement of the locking collar internal threads 62 with the external threads 144 of the female luer connector 140.

The flexibility and/or compliance of the locking collar 50 allows the locking collar 50 to self-adjust to minor dimensional differences of various female luer connectors 140, and still impart a slight friction between the components. The connection and disconnection of the two connectors is still easily made in the normal manner by manually turning the locking collar 50, but the slight friction between the locking collar internal threads 62 and the external threads 144 of the female luer connector 140 increases resistance to relative rotation, and thus can prevent accidental disconnection. This is advantageous when compared to some prior art male luer connectors that are more rigid. Due to their rigidity, the prior art male luer connectors are typically formed having sufficiently large tolerances to accommodate the minor dimensional differences of various female luer connectors. As a result, the engagement between the prior art male luer connectors and the female luer connectors tends to be less secure.

Figure 8:
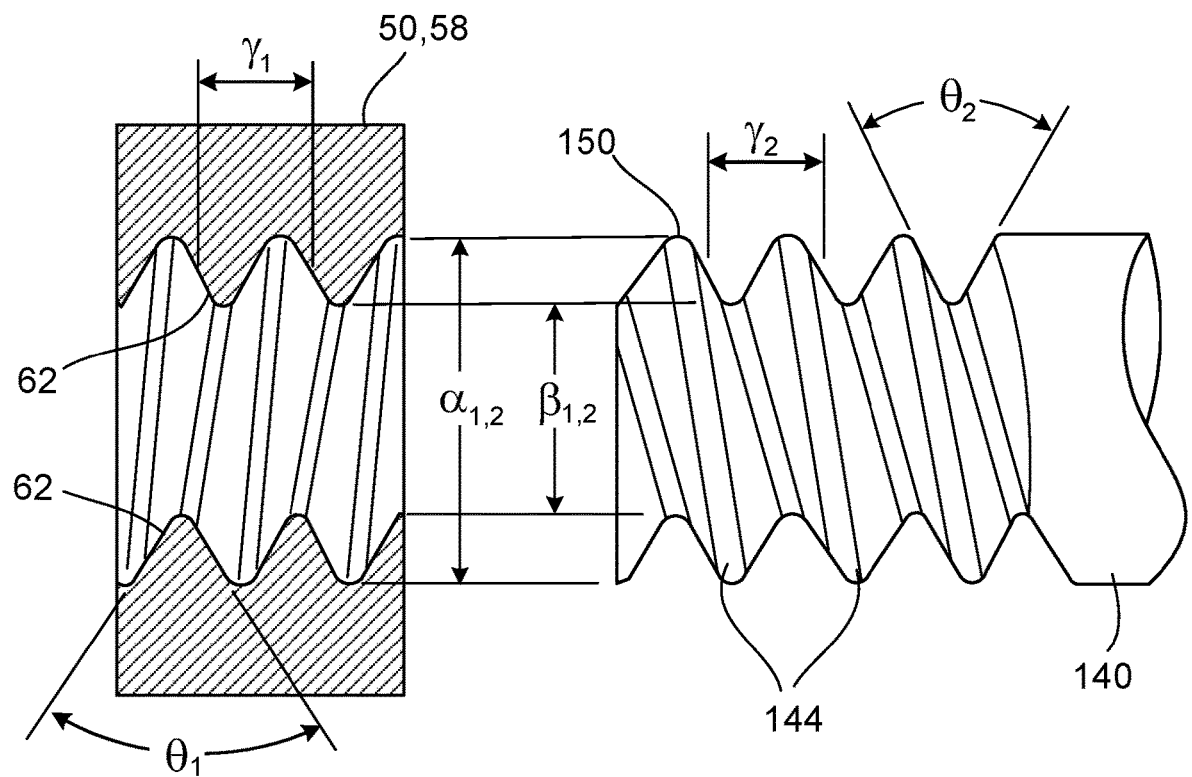
FIG. 8 is an enlarged view of the threaded portions of the locking collar and female luer connector illustrating thread definitions as used herein.

To still further improve connection security between the male luer connector 10 and the female luer connector 140, in some embodiments, the internal threads 62 of the locking collar 50 are shaped and/or dimensioned to provide slight interference when engaged with the external threads 144 of the female luer connector 140. For example, the locking collar internal threads 62 may be formed having a thread angle θ1 (FIG. 8) that is greater than the thread angle θ2 of the external threads 144 of the female luer connector 140. In another example, the locking collar internal threads 62 may be formed having a slightly different pitch γ1 than the pitch γ2 of the external threads 144 of the female luer connector 140. In another example, the major diameter α1 of the locking collar second end 58 (e.g., the inner diameter of the locking collar second end 58) is slightly less than the major diameter α2 of the external threads 144 of the female luer connector 140 (e.g., the outer diameter of the female luer connector first end 150). Since the internal threads 62 of the locking collar 50 are shaped and/or dimensioned to provide slight interference when engaged with the external threads 144 of the female luer connector 140, the relatively compliant locking collar internal threads 62 are further deformed when engaged with the female luer connector external threads 144. As a result of the interference, friction between the locking collar internal threads 62 and the female luer connector external threads 144 is further increased, further increasing the resistance to rotation and allowing the locking collar 50 to remain more securely in place if the male luer connector 10 and the female luer connector 140 are inadvertently rotated during use.

Each of the male luer connector improvements described herein can be implemented individually or in various combinations to achieve improved fluid line connection security.

Although the male luer connector 10 has been described with respect to connection to a female luer connector 140 that accesses a patient's circulatory system via a catheter assembly during hemodialysis, the male luer connector 10 can be connected to other types of female luer connectors, and/or the female luer connector can provide connection to other access devices such as fistula needles.

The locking collar first end 56 is connected to the body 12 in a manner such that the collar 50 is retained in a desired axial position relative to the body 12, while the locking collar can rotate relative to the body 12 about the longitudinal axis 32. Although the cooperative engagement of the resilient fingers 60 with the collar seat 26 serves this function in the illustrated embodiment, the locking collar 50 may be connected to the body 12 using other structures that serve this function. For example, an outer surface of the body 12 may be formed having resilient members that engage a seat formed on an inner surface of the locking collar 50. In another example, an outer surface of the body 12 may be formed having an outwardly protruding annular flange, and the locking collar may receive the flange therewithin and include an inwardly extending lip that engages the flange and retains the locking collar on the body 12.

Although an embodiment was described in which the body 12 is formed of a material having a coefficient of friction that is less than the coefficient of friction of the material used to form the locking collar 50 so that the locking collar 50 rotates freely relative to the connector body 12, free rotation of the locking collar 50 relative to the connector body 12 can be achieved in other ways. For example, in some embodiments, the locking collar 50 is formed of a material having a coefficient of friction that is less than (e.g., about 0.2 to about 0.4 less than) the coefficient of friction of the material used to form the body 12. In another example, in some embodiments, both the locking collar 15 and the body 12 are formed of materials that have a low coefficient of friction. In some embodiments, the coefficient of friction of the materials used to form both the body 12 and the locking collar are in the range of 0.1 to 0.3. In this case, the materials used to form the body 12 may be, but are not required to be, the same as the materials used to form the locking collar 50 as long as both are formed of materials having a low coefficient of friction.

Although an implementation was described in which the locking collar 50 is formed of a material that is more flexible than the material used to form the female luer connector 140 to allow the collar threads 62 to deform when engaged with the female luer connector external threads 144, increasing the flexibility of the locking collar 50 (for example, to be more flexible than the female luer connector 140) can be achieved by other techniques. For example, in some implementations, the locking collar material is conventional, and the locking collar shape is modified to increase the flexibility of the locking collar 50 by reducing the wall thickness of the locking collar 50.

A number of embodiments have been described. Nevertheless, it will be understood that various modifications may be made without departing from the spirit and scope of the disclosure. Accordingly, other embodiments are within the scope of the following claims.

What is claimed is:

1. A male fluid line connector configured to engage a female fluid line connector, the male fluid line connector comprising:
   a body including:
      a first end configured to be connected to a fluid line,
      a tapered second end opposed to the first end, the tapered second end configured to be inserted into and form a fluid-tight connection with the female fluid line connector,
      a body longitudinal axis that extends between the first end and the tapered second end, and
      a collar seat disposed between the first end and the tapered second end, and
   a locking collar, the locking collar comprising:
      an internal thread,
      a locking collar first end, and
      a locking collar second end opposed to the locking collar first end,
   wherein the locking collar first end comprises a plurality of resilient fingers positioned radially inward of an annular outer surface of the locking collar, the annular outer surface radially surrounding the plurality of resilient fingers, the plurality of resilient fingers tapered so as to extend radially inward at an angle with respect to the annular outer surface, the annular outer surface and the plurality of resilient fingers defining an annular space between one another wherein the plurality of resilient fingers can deflect, the locking collar connected to the body in a manner such that the plurality of resilient fingers of the locking collar are retained by the collar seat to prevent axial travel of the locking collar relative to the body along the body longitudinal axis while the plurality of resilient fingers of the locking collar are rotated relative to the body about the body longitudinal axis, the locking collar second end configured to engage an outer surface of the female fluid line connector.

2. The male fluid line connector of claim 1, wherein the locking collar internal thread is configured to engage a corresponding thread provided on the outer surface of the female fluid line connector, the locking collar internal thread configured to deform when engaged with the corresponding thread provided on the outer surface of the female fluid line connector.

3. The male fluid line connector of claim 2, wherein the locking collar internal thread has a non-zero thread angle that is greater than a non-zero thread angle of the corresponding thread provided on the outer surface of the female fluid line connector.

4. The male fluid line connector of claim 2, wherein a major diameter of the locking collar internal thread is less than a major diameter of the corresponding thread provided on the outer surface of the female fluid line connector.

5. The male fluid line connector of claim 1, wherein the locking collar is more flexible than the female fluid line connector.

6. The male fluid line connector of claim 1, wherein the locking collar is formed of a material that is more flexible than a material used to form the female fluid line connector.

7. The male fluid line connector of claim 1, wherein the locking collar has a durometer value that is less than a durometer value of the female fluid line connector on a given durometer scale.

8. The male fluid line connector of claim 1, wherein an interior surface of the locking collar includes a region that engages a region of the outer surface of the female fluid line connector, and the region of the locking collar has a maximum inner diameter that is less than a maximum outer diameter of the region of the outer surface of the female fluid line connector.

9. The male fluid line connector of claim 1, wherein the locking collar includes through holes that are elongated in a direction parallel to the body longitudinal axis, the through holes extending between an interior surface of the locking collar and an exterior surface of the locking collar and through the internal thread, wherein each through hole is spaced apart from the adjacent through holes along a circumference of the locking collar, wherein the locking collar first end comprises a first end face and the locking collar second end comprises a second end face, the through holes spaced from the first end face and the second end face so as not to extend through the first end face or the second end face.

10. The male fluid line connector of claim 1, wherein the body is formed of a material having a coefficient of friction in a range of 0.1 to 0.3.

11. The male fluid line connector of claim 1, wherein the tapered second end of the body does not protrude beyond a plane that is transverse to the body longitudinal axis and includes an end face of the locking collar.

12. The male fluid line connector of claim 11, wherein the internal thread of the locking collar is arranged to begin at a predetermined distance from the locking collar end face, and the predetermined distance is selected so that when the tapered second end of the body is inserted into the female fluid line connector, a leading edge of a corresponding thread provided on the outer surface of the female fluid line connector abuts a leading edge of the internal thread of the locking collar before an outer surface of the tapered second end of the body forms a connection with an internal surface of the female fluid line connector.

13. The male fluid line connector of claim 11, wherein the tapered second end of the body is recessed within the locking collar.

14. The male fluid line connector of claim 1, wherein the body is formed of a material comprising acrylic and wherein the locking collar is formed of a material comprising polypropylene.

15. The male fluid line connector of claim 1, wherein the tapered second end of the body is configured to form a luer-slip connection with the female fluid line connector.

* * * * *